US008852870B2

(12) United States Patent
Vetvicka et al.

(10) Patent No.: US 8,852,870 B2
(45) Date of Patent: Oct. 7, 2014

(54) SYSTEMS AND METHODS FOR DIAGNOSIS AND PROGNOSIS OF CANCER

(75) Inventors: Vaclav Vetvicka, Louisville, KY (US); Martin Fusek, Tursko (CZ); Jarmila Zidkova, Prague (CZ)

(73) Assignee: University of Louisville Research Foundation, Inc., Louisville, KY (US)

( * ) Notice: Subject to any disclaimer, the term of this patent is extended or adjusted under 35 U.S.C. 154(b) by 400 days.

(21) Appl. No.: 12/999,389

(22) PCT Filed: Jun. 16, 2009

(86) PCT No.: PCT/US2009/047504
§ 371 (c)(1),
(2), (4) Date: Dec. 16, 2010

(87) PCT Pub. No.: WO2010/005718
PCT Pub. Date: Jan. 14, 2010

(65) Prior Publication Data
US 2011/0081669 A1  Apr. 7, 2011

Related U.S. Application Data

(60) Provisional application No. 61/061,834, filed on Jun. 16, 2008.

(51) Int. Cl.
*G01N 33/53* (2006.01)
*G01N 33/574* (2006.01)
*G01N 33/564* (2006.01)

(52) U.S. Cl.
CPC ............ *G01N 33/574* (2013.01); *G01N 33/564* (2013.01); *G01N 2333/96416* (2013.01)
USPC .......................................... 435/7.1; 435/7.23

(58) Field of Classification Search
CPC .......... G01N 33/574; G01N 33/57488; G01N 2800/00
See application file for complete search history.

(56) References Cited

U.S. PATENT DOCUMENTS

| 5,501,969 A | 3/1996 | Hastings et al. |
| 5,800,814 A | 9/1998 | Fusek et al. |
| 2002/0165355 A1* | 11/2002 | Meheus et al. ............... 530/350 |
| 2007/0083334 A1 | 4/2007 | Mintz et al. |
| 2008/0108084 A1 | 5/2008 | Robertson et al. |

OTHER PUBLICATIONS

Bosscher et al., Gynecologic Oncology, 2001, 81, 138-143.*
Cancer information from National Institute of Cancer, Apr. 29, 2010, pp. 1-2.*
Vogelstein et al. Nature Medicine, 2004, 10(8): 789-799.*
Barthell et al. "Immunohistochemical visualization of cathepsin-D expression in breast cancer," 2007, Anticancer Res., vol. 27, pp. 2035-2040.
Bazzett et al. "Modulation of proliferation and chemosensitivity by pCD and its peptides in ovarian cancer," Gynecol Oncol., 1999, vol. 74, pp. 81-187.
Benes et al., "Detection of procathepsin D in rat milk," Comp. Biochem Physiol., 2002, vol. 133, pp. 113-118.
Benes et al. "Effect of procathepsin D activation peptide on gene expression of breast cancer cells," Cancer Letters, 2006, vol. 239, pp. 46-54.
Bosscher et al., "Epitope Recognition by Anti-Cathepsin D Autoantibodies in Endometrial Cancer," Gynecologic Oncology, 2001, vol. 81(2), pp. 138-143.
Fernandez-Aguilar et al., "Expression of cathepsin D and galectin 3 in tubular carcinomas of the breast," APMIS, 2008, vol. 116, pp. 33-40.
Ferrandina et al., "Relationship between cathepsin-D content and disease free survival in node-negative breast cancer patients: A meta-analysis," Br J Canc, 1997, vol. 76, pp. 661-666.
Fusek et al., "Dual Role of Cathepsin D: Ligand and Protease," Biomed Papers, 2005, vol. 149(1), pp. 43-50.
Fusek et al., "Mitogenic function of human procathepsin D: The role of the propeptide," Biochem J, 1994, vol. 303, pp. 775-780.
Fusek et al., "Secretion of Cytokines in Breast Cancer Cells: The Molecular Mechanism of Procathepsin D Proliferative Effects," Journal of Interferon & Cytokine Research, 2007, vol. 27, pp. 191-199.
Glondu et al., "Down-regulation of cathepsin-D expression by antisense gene transfer inhibits tumor growth and experimental lung metastasis of human breast cancer cells,"Oncogene, 2002, vol. 21, pp. 5127-5134.
Harris et al., "American Society of Clinical Oncology 2007 Update of recommendation for the use of tumor markers in breast cancer," J Clin. Oncol, 2007, vol. 25, pp. 5287-5312.
Kaneko et al., "Immunohistochemical molecular markers as predictors of curability of endoscopically resected submucosal colorectal cancer," World J. Gastroenterol, 2007, vol. 13, pp. 3829-3835.
Koelsch et al., Human procathepsin D: three-dimensional model and isolation. In: Aspartic Proteinases: Structure, Function, Biology, and Biomedical Implications, 1995, Plenum Press, New York, K. Takahashi, editor, pp. 273-278.
Kristek et al., "Tumor growth fraction, expression of estrogen and progesterone receptors, p53, Bcl-2 and cathepsin D activity in primary ductal invasive breast carcinoma and their axillary lymph node metastases," Coll. Antropol, 2007, vol. 4, pp. 043-1047.
Leto et al., "Cathepsin D expression levels in nongynecological solid tumors: clinical and therapeutical implications," Clin. Exp. Metastasis., 2004, vol. 21, pp. 91-106.
Lou et al., "Cathepsin D is secreted from M-BE cells: Its potential role as a biomarker of lung cancer," J Proteome Res, 2007, vol. 6, pp. 1083-1092.
Minarowski et al., "The activity of cathepsin D in saliva of cystic fibrosis patients," Fol Histol Cytobiol, 2007, vol. 45, pp. 165-168.

(Continued)

*Primary Examiner* — Hong Sang
(74) *Attorney, Agent, or Firm* — Stites & Harbison PLLC; Terry L. Wright

(57) ABSTRACT

Methods for diagnosing a cancer in a subject are provided that include determining an amount of autoantibodies immunoreactive to procathepsin D (pCD) in a sample obtained from the subject. Further provided are systems for diagnosing a cancer in a subject that include an autoantibody immunoreactive pCD antigen and a means for detecting binding of an autoantibody to the antigen.

9 Claims, 3 Drawing Sheets

(56) References Cited

OTHER PUBLICATIONS

Ohri et al., "Depletion of procathepsin D gene expression by RNA interference—A potential therapeutic target for breast cancer," Cancer Biology and Therapy, 2007, vol. 6, pp. 1081-1087.

Ohri et al., "Procathepsin D expression correlates with invasive and metastatic phenotype of MDA-MB-231 derived cell lines," J Biol Macromol, 2007, vol. 41, pp. 204-209.

Posnett et al., "A novel method for producing anti-peptide antibodies," J Biol Chem, 1988, vol. 263, pp. 1719-1725.

Reid et al., "Immunolocalization of cathepsin D in normal and neoplastic tissues," J Clin Pathol, 1986, vol. 39, pp. 1323-1330.

Saraswat-Ohri et al., "The propeptide of cathepsin D increases proliferation, invasion and metastasis of breast cancer cells," International Journal of Oncology, 2008, vol. 32, pp. 491-498.

Tam, JP., "Synthetic peptide vaccine design: synthesis and properties of a high-density multiple antigenic peptide system," PNAS USA, 1988, vol. 85, pp. 5409-5413.

Thorpe et al., "Association between high concentration of 52,000 MW cathepsin D and poor prognosis in primary human breast cancer," Cancer Res, 1989, vol. 49, pp. 6008-6014.

Vagner et al., "Colour-monitored solid-phase, multiple peptide synthesis under low-pressure continuous-flow conditions. Synthesis of Medium-size Peptides: The propart of human procathepsin D and the growth-hormone releasing factor," Coll. Czech. Chem. Commun., 1993, vol. 58, pp. 435-444.

Vashishta et al., "Possible role of procathepsin D in human cancer," Fol. Microbiol., 2005, vol. 50, pp. 71-76.

Vashista et al., "Ribozyme-targeting procathepsin D and its effect on invasion and growth of breast cancer cells: An implication in breast cancer therapy," Int J Oncol, 2007, vol. 30, pp. 1112-1130.

Vashishta et al., "Role of Activation Peptide of Procathepsin D in Proliferation and Invasion of Lung Cancer Cells," Anticancer Research, 2006, vol. 26, pp. 4163-4170.

Vashishta et al., "Procathepsin D Secreted by HaCaT keratinocyte cells—A novel regulator of keratinocyte growth," European Journal of Cell Biology, 2007, vo.. 86, pp. 303-313.

Vaupel et al., "Blood Flow, Oxygen and Nutrient Supply, and Metabolic Microenvironment of Human Tumors: A Review," Cancer Res, 1989, vol. 49, pp. 6449-6465.

Vetvicka et al., "Procathepsin D in breast cancer: What do we know? Effects of ribozymes and other inhibitors," Cancer Gene Therapy, 2000, vol. 9, pp. 854-863.

Vetvicka et al., "Procathepsin D and human cancer," Current Topics in Peptide & Protein Research, 2004, vol. 6, pp. 93-99.

Vetvicka et al., "Anti-human pCD activation peptide antibodies inhibit breast cancer development," Breast Cancer Res Treatment, 1999, vol. 57, pp. 261:269.

Vetvicka et al., "Effect of pCD and its activation peptide on prostate cancer cells," Cancer Lett, 1998, vol. 129, pp. 55-59.

Vetvicka et al., "Analysis of the interaction of procathepsin D activation peptide with breast cancer cells," Int J Cancer, 1997, vol. 73, pp. 403-409.

Vetvicka et al., "Role of enzymatically inactive pCD in lung cancer," Int. J. Cancer, 2004, vol. 24, pp. 2739-2744.

Vetvicka et al., "Analysis of the interaction of the procathepsin D activation peptide with breast cancer cells," Int J Cancer, 1997, vol. 73, pp. 403-409.

Vetvicka et al., "Role of procathepsin D activation peptide in prostate cancer growth," Prostate, 2000, vol. 44, pp. 1-7.

Vetvicka et al., "Human breast milk contains procathepsin d—detection by specific antibodies," Biochem Molec Biol Int, 1993, vol. 30, pp. 921-928.

Vignon et al., "Autocrine growth stimulation of the MCF 7 breast cancer cells by the estrogen-regulated 52 K protein," Endocrinology, 1986, vol. 118, pp. 1537-1545.

Wang et al., "Long-term high-titer neutralizing activity induced by octameric synthetic HIV antigen," Science, 1991, vol. 254, pp. 285-288.

USPTO/ISR, International Search Report and Written Opinion in related international application No. PCT/US09/47504, mailed Oct. 9, 2009.

* cited by examiner

Pre – Pro – Cathepsin D

Pro – Cathepsin D (53 kDa)

Cathepsin D – single chain (41 kDa)

Cathepsin D – two chain (light 14 kDa and heavy 31 kDa)

Active Site

Glycosylation sites

SYSTEMS AND METHODS FOR DIAGNOSIS AND PROGNOSIS OF CANCER

RELATED APPLICATIONS

This application claims priority from U.S. Provisional Application Ser. No. 61/061,834, filed Jun. 16, 2008, the disclosure of which is incorporated herein by reference in its entirety.

GOVERNMENT INTEREST

This invention was made with government support under Grant No. CA082159 awarded by the National Institutes of Health. The government has certain rights in the invention.

TECHNICAL FIELD

The presently-disclosed subject matter relates to systems and methods for diagnosis and prognosis of cancer. In particular, the presently-disclosed subject matter relates to diagnostic and prognostic methods that include a determination of an amount of autoantibodies immunoreactive to procathepsin D (pCD) in a biological sample from a subject.

BACKGROUND

Despite the recent progress that has been made in the diagnosis and treatment of various cancers, the long-term survival rate for cancer patients has not changed significantly in the last decade as the clinical outcome of a particular cancer is usually based on timely diagnosis. For example, Stage I ovarian cancer can typically be cured in 90% of all cases, while the five-year survival rate for patients with advanced forms of this disease (e.g., Stage III or IV) is less than 21%. As such, the prospects for significant improvements in cancer survival reside in early diagnosis.

Current diagnostic assays for many cancers are antigen-based and rely on the detection of circulating proteins that are associated with the particular cancer. These assays rely on the expression, synthesis, and release of specific proteins by cells (e.g., tumor cells) either by active secretion or shedding, or as a consequence of cell death (either necrosis or apoptosis). As such, these antigenic proteins must "escape" the primary site of disease, saturate the antigen-processing capacity of the individual's immune components, gain access to the circulation, and reach a sufficient steady-state concentration to be detected by enzyme- or radio label-based immunoassays. These events usually occur well after the initial establishment of disease (e.g., a neoplastic transformation event and tumor foci development). Thus, and despite the fact that certain specific antigenic epitopes exhibit common recognition among patients with the same tumor types, the use of these antigen-based cancer assays have not been widely accepted into clinical practice and many individual countries differ in the use of these potential diagnostic factors.

One such antigen, which has not been widely accepted as a reliable marker for cancer detection and diagnosis, is cathepsin D (CD). Increased levels of CD were first reported in several human neoplastic tissues more than 20 years ago (Reid, et al. 1986). Several years later, the first clinical studies found CD related to metastasis-free survival and disease-free survival in breast cancer patients (Thorpe, et al. 1989). Since then, numerous clinical studies have suggested a connection between CD levels and prognosis, incidence of metastasis, tumor aggressiveness and the degree of chemoresistance in a variety of solid tumors (Leto, et al. 2004; Ferrandina, et al. 1997). Other studies, however, have found conflicting results regarding the use of CD as a marker for cancer by employing different methodologies for CD quantification, different criteria for patient and diagnosis selection, and different durations of follow-up periods (Leto, et al. 2004). Additionally, previous studies that have examined the diagnostic and prognostic value of CD in cancer have been further complicated by the fact that there are several forms of CD in a tissue at the same time including procathepsin D (pCD), intermediate enzymatically active CD, mature heavy and light chain CD, as well as different forms of post-translationally modified pCD.

The roles of these additional forms of CD in cancer development have also been investigated. For example, the mitogenic effect of secreted pCD on breast cancer cells was first proposed over 20 years ago (Vignon, et al. 1986). Since that time, studies have demonstrated that pCD secreted from cancer cells serves as an autocrine growth factor for breast (Fusek and Vetvicka, 1994), prostate (Vetvicka, et al. 1998), ovarian (Bazzett et al. 1999) and lung cancer cells (Vetvicka, et al. 2004). Further, breast cancer cells with down-regulated expression of pCD by either antisense gene transfer (Glondu, et al. 2002), RNA interference (Ohri, et al. 2007) or ribozymes (Vashishta, et al. 2007) have displayed reduced growth in vitro and in vivo. Tumor growth has also been shown to be inhibited by anti-pCD antibodies in vivo and in vitro (Vetvicka, et al. 1997), and it has also been found that binding to cancer cells as well as pCD mitogenic potential is blocked by antibodies specific for the propeptide part of pCD (Vetvicka, et al. 1999).

Despite the extensive research into CD and pCD, and their respective roles in cancer, the use of CD or pCD, as a reliable marker for the detection and diagnosis of cancer still remains controversial. Indeed, some recent studies have suggested that CD may be used as a marker in lung cancer (Lou, et al. 2007) and colorectal cancer (Kaneko, et al. 2007), whereas other studies examining the role of CD in breast cancer have found exactly the opposite results (Kristek, et al. 2007; Fernandez-Aguilar and Noel, 2008) or only a questionable correlation between CD and cancer (Barthelli, et al. 2007). These insufficient and inconsistent findings recently led the American Society of Clinical Oncology not to recommend the use of CD as a tumor marker in breast cancer (Harris, et al. 2007).

SUMMARY

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments of the presently-disclosed subject matter, a method for diagnosing a cancer is provided. In some embodiments, the method comprises: providing a biological sample from a subject; determining an amount in the sample of autoantibodies immunoreactive to procathepsin D (pCD); and comparing the amount of the autoantibodies in the sample, if present, to a control level of the autoantibodies. In some embodiments, the subject can then be diagnosed as having the cancer is there is a measurable difference in the amount of autoantibodies in the sample as compared to the control level.

In some embodiments of the presently-disclosed methods, a method for diagnosing a cancer is provided that further comprises selecting or modifying a treatment for the cancer based on the determined amount of the autoantibodies. In some embodiments, a method for diagnosing a cancer is provided that further comprises characterizing a cancer based on the determined amount of autoantibodies. In some embodiments, characterizing the cancer comprises determining a stage of the cancer.

In some embodiments of the presently-disclosed subject matter, the cancer is selected from breast cancer, lung cancer, ovarian cancer, colon cancer, rectal cancer, and cervical cancer. In some embodiments, the cancer is breast cancer. In some embodiments of the presently-disclosed subject matter, the biological sample comprises blood, plasma, serum, urine, cerebrospinal fluid, saliva, or breast milk.

In some embodiments of the presently-disclosed methods, determining an amount in the sample of autoantibodies immunoreactive with pCD comprises determining the amount in the sample of the autoantibodies through the use of an immunoassay analysis. In some embodiments, the immunoassay analysis comprises an enzyme-linked immunosorbent assay (ELISA). In some embodiments, the determining the amount in the sample of the autoantibodies comprises: contacting an antigen, which comprises a pCD polypeptide or fragment thereof, with the sample; and detecting autoantibodies in the sample that are immunoreactive to the antigen.

In some embodiments of the presently-disclosed subject matter, the antigens which are bound by autoantibodies immunoreactive to pCD comprise a pCD activation peptide or a fragment thereof. In some embodiments, the antigen comprises a polypeptide of SEQ ID NO: 1 or a polypeptide of SEQ ID NO: 2. In some embodiments, the antigen comprises a plurality of polypeptides of SEQ ID NO: 2.

Further provided, in some embodiments of the presently-disclosed subject matter, are systems for diagnosing a cancer in a subject. In some embodiments, a system is provided that comprises: an autoantibody immunoreactive peptide antigen that comprises a pCD polypeptide or fragment thereof; a container for containing the antigen; and a means for detecting binding of an autoantibody to the antigen, where the autoantibody is from a biological sample that has been obtained from a subject. In some embodiments, the antigen can be attached to a support, such as, in some embodiments, a microtiter plate, a membrane, a polystyrene bead, a test tube, or a dipstick.

In some embodiments of the presently-disclosed systems, the means for detecting binding of the autoantibody includes an antibody preparation that binds to the autoantibody. In some embodiments, the antibody preparation comprises a detectable label. In some embodiments, the detectable label comprises a radiolabel, an enzyme, biotin, a fluorescent tag, a hapten, or a luminescent label.

Advantages of the presently-disclosed subject matter will become evident to those of ordinary skill in the art after a study of the description, Figures, and non-limiting Examples in this document

BRIEF DESCRIPTION OF THE SEQUENCE LISTING

Figure 1:
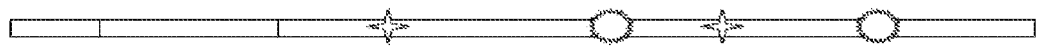
FIG. 1 is a schematic diagram of various members of the cathepsin D family of aspartic proteinases, including pre-procathepsin D, procathepsin D, cathepsin D (single chain), and cathepsin D (heavy and light chains), and depicting removal of various portions of the polypeptide as well as depicting active and glycosylation sites on the polypeptides.
Figure 1:
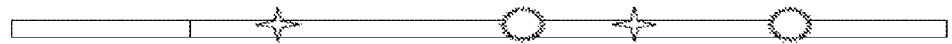
Figure 1:
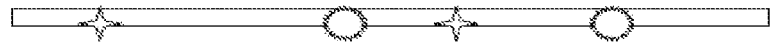
Figure 1:
Figure 1:
Figure 1:

SEQ ID NO: 1 is an amino acid sequence of an activation peptide of procathepsin D.
SEQ ID NO: 2 is an amino acid sequence of a fragment of an activation peptide of procathepsin D.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. Unless otherwise indicated or apparent, the references to the GENBANK® database are references to the most recent version of the database as of the filing date of this Application.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The terms "polypeptide", "protein", and "peptide", which are used interchangeably herein, refer to a polymer of the 20 protein amino acids, including modified amino acids (e.g., phosphorylated, glycated, etc.) and amino acid analogs, regardless of size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein", "polypeptide" and "peptide" are used interchangeably herein when referring to a gene product and fragments thereof. Thus, exemplary polypeptides include gene products, naturally-occurring proteins, homo logs, orthologs, paralogs, fragments and other equivalents, variants, fragments, and analogs of the foregoing.

The terms "polypeptide fragment" or "fragment", when used in reference to a polypeptide, refers to a polypeptide in which amino acid residues are absent as compared to the full-length polypeptide itself, but where the remaining amino acid sequence is usually identical to the corresponding positions in the reference polypeptide. Such deletions can occur at the amino-terminus or carboxy-terminus of the reference polypeptide, or alternatively both. A fragment can retain one or more of the biological activities of the reference polypeptide, including antigenic properties. In some embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived. When the term "peptide" is used herein, it is intended to include the full-length peptide as well as fragments of the peptide.

Cathepsin D (CD) is an aspartic protease found in lysosomes of all mammalian cells, and is considered to be one of the main catabolic proteinases. CD is a proteinase with pH optimum close to 3, and its activity rapidly falls at pH above 5. In the form of a zymogen, CD is targeted via the mannose 6-phosphate (M6P) pathway. The two M6P receptors involved in the lysosomal targeting are localized both intra- cellularly and on the outer cell membrane. Two roles were identified for the cation-independent M6P receptor present on the cellular surface, including recognizing molecules which contain the M6P tag and recapturing them, and binding and mediating the effect of the insulin-like growth factor II (IGF II).

"Procathepsin D" or "pCD" is the precursor form of the lysosomal proteinase CD, such as for example human pCD (GENBANK® Accession no. NP_001900). pCD is typically secreted from cultured human cell lines at a low level. However, in response to estrogen stimulation, pCD becomes the major secreted protein in several human breast cancer cell lines. Detailed analysis of the pCD gene regulating elements have revealed a combination of both housekeeping and regulated promoter types, and have suggested that pCD expression can also be controlled by estrogen under some physiological conditions as well. Indeed, increased levels of cathepsin D were previously detected during mammary gland involution in rats and a steroid regulated production has been described in the rat uterus. The presence of intact pCD has also been reported in bovine and human milk.

The activation of pCD is accomplished by the removal of the 44 amino acid activation peptide at the N-terminus of the proenzyme, which generally takes place at the low pH of lysosomes and is achieved by a combination of limited autoproteolysis and cleavage by other lysosomal proteinases. Details regarding the proteolytic activity of pCD in the extracellular space have yet to be reported. Nevertheless, tissues with high consumption of energy, as in the case of tumor tissues, can locally produce a low pH environment, and consequently allow the activation of a secreted pCD.

According to the three-dimensional model of the pCD structure, the propeptide portion, which is referred to herein as the "activation peptide" or "AP," is localized on the surface of the pCD molecule. Using synthetic peptides corresponding to different parts of the AP, the region responsible for binding of pCD to the cancer cell surface has been shown to be localized between residues 36-44 of the AP (Vetvicka, et al. 1997).

The present invention is based on the investigation of the role of aspartic enzyme cathepsin D in development of cancer, including how the enzymatically inactive proenzyme pCD is responsible for the biological effects. Briefly, pCD is released from cancer cells and subsequently binds back exclusively to the surrounding cancer cells, thus stimulating their proliferation. It has now been surprisingly determined that cancers can be diagnosed and characterized by the production of autoantibodies to pCD in the afflicted subject. That is, the immune system of the subject afflicted with a cancer is stimulated to produce antibodies against self-antigens, as opposed to foreign antigens, and in particular pCD. The presently-disclosed subject matter provides systems and methods for the collection and measurement of anti-pCD autoantibodies for use in diagnosing and characterizing cancers.

In some embodiments of the presently-disclosed subject matter, a method for diagnosing a cancer in a subject is provided. The terms "diagnosing" and "diagnosis" are used herein to refer to methods by which the skilled artisan can estimate and even determine whether or not a subject is suffering from a given disease or condition. The skilled artisan often makes a diagnosis on the basis of one or more diagnostic indicators, such as, for example, autoantibodies immunoreactive to pCD, the amount (including presence or absence) of which is indicative of the presence, severity, or absence of the condition.

Along with diagnosis, clinical disease prognosis is also an area of great concern and interest. It is important to know the stage and rapidity of advancement of a cancer in order to plan the most effective therapy. If a more accurate prognosis can be made, appropriate therapy, and in some instances less severe therapy for the patient can be chosen. Measurement of amounts of autoantibodies immunoreactive with pCD, as disclosed herein, can be useful in order to categorize subjects according to advancement of a specific type of cancer who will benefit from particular therapies and differentiate from other subjects where alternative or additional therapies can be more appropriate.

As such, "making a diagnosis" or "diagnosing", as used herein, is further inclusive of determining a prognosis, which can provide for predicting a clinical outcome (with or without medical treatment), selecting an appropriate treatment (or whether treatment would be effective), or monitoring a current treatment and potentially changing the treatment, based on the measure of levels of autoantibodies immunoreactive to pCD disclosed herein.

The phrase "determining a prognosis" as used herein refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the presence, absence, or levels of autoantibodies immunoreactive to pCD. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting a cancer (e.g., not expressing the autoantibodies immunoreactive to pCD or expressing them at a reduced level), the chance of a given outcome may be about 3%. In certain embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an adverse outcome is a statistical analysis. For example, a level of autoantibodies immunoreactive to pCD (e.g., quantity of the autoantibodies in a sample) of greater than a control level in some embodiments can signal that a subject is more likely to suffer from a cancer than subjects with a level less than or equal to the control level, as determined by a level of statistical significance. Additionally, a change in autoantibody concentration from baseline levels can be reflective of subject prognosis, and the degree of change in the autoantibody level can be related to the severity of adverse events. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9%, and 99.99%, while preferred p values are 0.1, 0.05, 0.025, 0.02, 0.01, 0.005, 0.001, and 0.0001.

In some embodiments, a threshold degree of change in the level of an autoantibody immunoreactive to pCD can be established, and the degree of change in the level of the autoantibody in a biological sample can simply be compared to the threshold degree of change in the level. A preferred threshold change in the level of autoantibodies of the presently-disclosed subject matter is about 5%, about 10%, about 15%, about 20%, about 25%, about 30%, about 50%, about 75%, about 100%, and about 150%.

In some embodiments, a "nomogram" can be established, by which a level of an autoantibody immunoreactive to pCD can be directly related to an associated disposition towards a given outcome. The skilled artisan is acquainted with the use of such nomograms to relate two numeric values with the understanding that the uncertainty in this measurement is the same as the uncertainty in the autoantibody concentration because individual sample measurements are referenced, not population averages.

In some embodiments of the presently-disclosed subject matter, multiple determinations of an amount of autoantibodies immunoreactive to pCD can be made, and a temporal change in the amounts can be used to monitor the progression of a cancer and/or efficacy of appropriate therapies directed against the cancer. In such an embodiment, for example, one might expect to see a decrease or an increase in the autoantibodies over time during the course of effective therapy. Thus, the presently-disclosed subject matter provides, in some embodiments, a method for determining treatment efficacy and/or progression of a cancer disease in a subject. In some embodiments, the method comprises determining an amount of autoantibodies immunoreactive to pCD that are associated with a cancer in biological samples collected from the subject at different time points and comparing the amounts of the autoantibodies in the samples collected at different time points. For example, a first time point can be selected prior to initiation of a treatment and a second time point can be selected at some time after initiation of the treatment. The amounts of autoantibodies immunoreactive to pCD can be measured in each of the samples taken from different time points and qualitative and/or quantitative differences noted. A change in the amounts of the autoantibodies from the first and second samples can be correlated with determining treatment efficacy and/or progression of the cancer in the subject. In some embodiments, a treatment for the cancer can be selected or modified based on the determined amount of the autoantibodies.

The terms "correlated" and "correlating," as used herein in reference to the measurement of autoantibodies immunoreactive to pCD, refers to comparing the presence or quantity of the autoantibodies in a subject to their presence or quantity in subjects known to suffer from, or known to be at risk of, a cancer; or in subjects known to be free of a cancer, i.e. "normal individuals". For example, an amount of autoantibodies immunoreactive to pCD in a biological sample can be compared to a level known to be associated with a specific type of cancer. The sample's autoantibody level is said to have been correlated with a diagnosis; that is, the skilled artisan can use the autoantibody level to determine whether the subject suffers from a specific type of cancer, and respond accordingly. Alternatively, the sample's autoantibody level can be compared to a control autoantibody level known to be associated with a good outcome (e.g., the absence of a cancer), such as an average level found in a population of normal subjects.

In certain embodiments, an autoantibody immunoreactive to pCD is correlated to a cancer by merely its presence or absence. In other embodiments, a threshold level of an autoantibody immunoreactive to pCD can be established, and the level of the autoantibody in a subject sample can simply be compared to the threshold level.

As noted, in some embodiments, multiple determination of amounts of autoantibodies immunoreactive to pCD can be made, and a temporal change in the amounts can be used to determine a diagnosis or prognosis. For example, an amount of an autoantibody immunoreactive to pCD can be determined at an initial time, and again at a second time. In such embodiments, an increase in the amounts from the initial time to the second time can be diagnostic of a particular type of a cancer, or a given prognosis. Likewise, a decrease in the amounts from the initial time to the second time can be indicative of a particular type of cancer, or a given prognosis. Furthermore, the degree of change of the amounts can be related to the severity of the cancer and future adverse events.

In some embodiments of the presently-disclosed subject matter, a method for diagnosing a cancer in a subject comprises providing a biological sample from the subject; determining an amount in the sample of autoantibodies immunoreactive to pCD; and comparing the amounts of the autoantibodies in the sample, if present, to a control level of the autoantibodies. In some embodiments, the subject can then be diagnosed as having the cancer if there is a measurable difference in the amount of the autoantibodies in the sample as compared to the control level.

With regard to the step of providing a biological sample from the subject, the term "biological sample", as used herein, refers to any body fluid or tissue potentially comprising autoantibodies immunoreactive to pCD, including, but not limited to: blood, plasma, serum, urine, cerebrospinal fluid, saliva, or breast milk. In some embodiments, for example, the biological sample can be a blood sample, a serum sample, a plasma sample, or sub-fractions thereof. In some embodiments, the biological sample can be a urine sample, a cerebrospinal fluid sample, a saliva sample, or a breast milk sample.

As used herein, the term "subject" includes both human and other animal subjects. As such, the presently-disclosed subject matter provides for the diagnosis and prognosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl (i.e., poultry, such as turkeys, chickens, ducks, geese, guinea fowl, and the like), as they are also of economic importance to humans. Thus, also provided is the treatment of livestock, including, but not limited to, domesticated swine, ruminants, ungulates, horses (including race horses), poultry, and the like.

In some embodiments of the presently-disclosed subject matter, a method for diagnosing a cancer in a subject is provided that further comprises characterizing the cancer based on the determined amount of autoantibodies immunoreactive with pCD. "Characterizing," as used herein in reference to the diagnostic methods of the presently-disclosed subject matter, can refer to detecting the presence of a specific type of cancer or determining the severity of a cancer, such as, in some embodiments, determining a stage of a cancer (e.g., Stage I, Stage II, Stage III, Stage IV, etc.). For example, an amount of autoantibodies immunoreactive to pCD in a biological sample can be compared to a level that is associated with a particular stage of a cancer such that the skilled artisan can use the autoantibody level to characterize the cancer as being of a particular stage, and respond accordingly. In some embodiments, when a stage of a cancer is determined according to the presently-disclosed subject matter, the subject is known to have a particular type of cancer (e.g., breast cancer, ovarian cancer) but the stage of the particular type of cancer is not known. In such embodiments, the presently-disclosed subject matter can be used to identify a stage (e.g., Stage I, Stage II, Stage III, Stage IV, etc.) of the particular type of cancer.

The term "cancer" as used herein refers to all types of cancer or neoplasm or malignant tumors found in animals, and in particular all solid tumors including carcinomas and sarcomas. Non-limiting examples of cancers that can be diagnosed with the present methods and systems include breast cancer, head and neck cancer, brain cancer, liver cancer, pancreatic cancer, lung cancer, prostate cancer, stomach cancer, ovarian cancer, colon cancer, rectal cancer, cervical cancer, and prostate cancer. In some embodiments, the cancer is selected from the group consisting of breast cancer, lung cancer, ovarian cancer, colon cancer, rectal cancer, and cervical cancer. In some embodiments, the cancer is breast cancer.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, ductal carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Turning now to the pCD antigens utilized in accordance with the presently-disclosed subject matter, in some embodiments, the pCD antigen utilized for detecting and/or quantitating pCD autoantibodies can be a full-length pCD polypeptide (e.g., human pCD, GENBANK Accession No. NP_001900). In some embodiments, the pCD can include a fragment of the pCD polypeptide that will bind pCD-reactive autoantibodies. For example, in some embodiments, the pCD antigen comprises the propeptide portion of pCD or, in other words, the Activation Peptide (AP) of pCD of a fragment thereof. In some embodiments, the pCD antigen can comprise an AP of the sequence of SEQ ID NO: 1. In other embodiments, the pCD antigen can comprise a fragment of the AP, such as, for example, a polypeptide of SEQ ID NO: 2. Each of these pCD antigens can be isolated from appropriate sources (e.g., cultured cells; See U.S. Pat. No. 5,800,814, which is incorporated herein by this reference) or can be synthesized by recombinant or chemical synthesis techniques, as is generally known is the art.

In some embodiments of the presently-disclosed subject matter, a pCD antigen can be provided that comprises a plurality of pCD antigens or fragments thereof. In some embodiments, the pCD antigen can comprise a plurality of polypeptides of SEQ ID NO: 2. For example, in some embodiments, a multiple antigenic peptide (MAP) can be provided wherein alpha- and gamma-amino functional groups of lysine are used to form a backbone to which multiple polypeptides (e.g., polypeptides of SEQ ID NO: 2) can be attached to form a MAP bearing multiple copies of the polypeptide epitope in a high molar ratio. See, e.g., Wang, et al. 1991; Posnett, et al. 1988; and Tam, 1988; each of which are incorporated herein by this reference.

Turning now to the step of determining an amount in a biological sample of autoantibodies immunoreactive to pCD, in some embodiments, determining the amount in the sample of the autoantibodies comprises: contacting a pCD antigen with a sample and detecting the autoantibodies in the sample that are immunoreactive to the antigen. Various methods known to those skilled in the art can be used to determine the amount of the one or more autoantibodies immunoreactive to pCD in the provided biological sample. The term "immunoreact" or "immunoreactive" as used herein with regard to antibody binding, is used to refer to the binding by the variable regions of antibodies to specific epitopes of the presented antigens.

As noted, in some embodiments of the methods disclosed herein, determining the amounts of autoantibodies immunoreactive to pCD in a biological sample can include binding the autoantibodies to an antigen comprising a pCD polypeptide or fragment thereof, and then detecting either the binding event or the presence of the autoantibody isolated from the biological sample. In some embodiments, the amounts of the autoantibodies in the provided samples are determined using an immunoassay analysis.

Any suitable immunoassay analysis for detecting the autoantibodies can be utilized in accordance with the presently-disclosed subject matter, including, but are not limited to: enzyme-linked immunosorbent assay (ELISA); radioimmunoassay (RIA); multiplex immunoassay; immunoprecipitation; immunoblotting including, for example, Western blotting and dot blotting; and competitive binding assays. Immunoassays, in their most simple and direct sense, are binding assays. Although various exemplary immunoassay analyses are described herein for use in accordance with the presently-disclosed subject matter, it will be readily appreciated by those of ordinary skill in the art that detection of an autoantibody immunoreactive to pCD is not limited to such techniques, and that fluorescence-activated cell sorting (FACS), immunohistochemical analyses, precipitin reactions, and other such immunodetection methods can also can be used in connection with the presently-disclosed subject matter. For further guidance regarding various immunodetection methods, see, e.g., Nakamura, et al. (In: Handbook of Experimental Immunology (4th Ed.), Weir et al. (eds). Vol. 1, Chapter 27, Blackwell Scientific Publ., Oxford, 1987), which is incorporated herein by this reference.

With regard to the presently-disclosed methods, in some embodiments, the use of an immunoassay analysis includes obtaining a sample suspected of containing an autoantibody and contacting the sample with a pCD antigen in accordance with the presently-disclosed subject matter under conditions effective to allow the formation of immunocomplexes. Contacting the particular biological sample with the antigen under such effective conditions and for a period of time sufficient to allow the formation of immune complexes (e.g., primary immune complexes) is generally a matter of combining the pCD antigen and the sample, and incubating the mixture for a period of time long enough for the antibodies to form immune complexes with the antigens presented. After this time, the antigen-antibody mixture can be washed to remove any non-specifically bound antibody species, allowing only those antibodies specifically bound within the primary immune complexes to be detected.

The detection of immunocomplex formation can be achieved through the application of numerous approaches. As will be understood by those skilled in the art, detection methods can be based upon the detection of a label or marker, such as any radioactive, fluorescent, biological, or enzymatic tags or labels of standard use in the art. U.S. Pat. Nos. concerning the use of such labels include 3,817,837; 3,850,752; 3,939,350; 3,996,345; 4,277,437; 4,275,149; 4,302,534; 4,366,241; 4,637,988; 4,786,594; 5,108,896; 5,229,302; 5,629,164 and 5,691,154; each of which are incorporated herein by reference. In some embodiments, one may find additional advantages through the use of a secondary binding ligand such as a second antibody or a biotin/avidin ligand binding arrangement, as is known in the art.

In some embodiments, the primary immune complexes can be detected by a second binding ligand that has binding affinity for the antigen or the antibody presented in the sample, either specifically or non-specifically (e.g., reactivity to Fc region of the autoantibodies). In these cases, the second binding ligand can be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any unbound labeled secondary antibodies or ligands, and the remaining label in the secondary immune complexes is then detected.

Other methods for the detection of autoantibodies immunoreactive to pCD can include the detection of primary immune complexes by a two step approach. A second binding ligand, such as an antibody, that has binding affinity for the antigen or autoantibody is used to form secondary immune complexes, as described above. The second binding ligand contains an enzyme capable of processing a substrate into a detectable product and, hence, amplifying a signal over time. After washing, the secondary immune complexes are thus contacted with substrate, permitting detection.

Competitive binding assays or competitive immunodetection can also be used to detect the autoantibodies specific for the pCD antigens. In this technique, a labeled-antibody is first incubated in solution with the antigen. Signal emitted by the label is measured. This is followed by contacting this antigen/antibody complex with a sample containing or suspected of containing the antibodies of interest. If the sample has antibodies specific to the antigen, they will bind the antigen and competitively displace the labeled-antibody. This can be detected as a drop in intensity of the signal from the label.

Although certain embodiments of the presently-disclosed methods only call for a qualitative assessment of the presence or absence of an autoantibody immunoreactive to pCD in the biological sample, other embodiments of the presently-disclosed methods call for a quantitative assessment of the amount of the autoantibodies in the biological sample. Such quantitative assessments can be made, for example, using one of the above mentioned methods, as will be understood by those skilled in the art. As such, in some embodiments of the presently-disclosed subject matter, a method for detecting and/or quantitating levels of autoantibodies in a subject is further provided.

In certain embodiments of the presently-disclosed subject matter, it can be desirable to include a control sample that is analyzed concurrently with the biological sample, such that the results obtained from the biological sample can be compared to the results obtained from the control sample. Additionally, it is contemplated that standard curves can be provided, with which assay results for the biological sample can be compared. Such standard curves present levels of autoantibodies as a function of assay units, i.e., fluorescent signal intensity, if a fluorescent signal is used. Using samples taken from multiple normal subjects, standard curves can be provided for control levels of the one or more autoantibodies in normal biological samples.

It is further contemplated that the efficacy, accuracy, sensitivity, and/or specificity of the methods can be enhanced by probing for additional known biomarkers in the biological sample. The analysis of autoantibodies can be carried out separately or simultaneously with additional markers within one test sample. For example, several markers can be combined into one test for efficient processing of a number of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker levels over time. Increases or decreases in marker levels, as well as the absence of change in marker levels, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of autoantibodies can be carried out in a variety of physical formats as well. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments of the presently-disclosed subject matter, a system for diagnosing a cancer in a subject is provided. In some embodiments, the system comprises: an autoantibody immunoreactive peptide antigen that comprises a pCD polypeptide or fragment thereof in accordance with the presently-disclosed subject matter; a container for containing the antigen; and a means for detecting binding of the autoantibody to the antigen. In some embodiments, such systems can be provided in the form of commercial kits that can be used to test a biological sample, or a series of biological samples, from a subject.

In some embodiments, the means for detecting binding of the autoantibody to the pCD antigen can comprise an antibody preparation that binds to the autoantibody. For example, in some embodiments, the means for detecting binding of the autoantibody can be a secondary antibody capable of forming a secondary immune complex with a primary immune complex that includes the autoantibody and pCD antigen. In some embodiments, the antibody preparation can further comprise a detectable label that is associated, or linked to, the detecting antibody preparation. In some embodiments, such detectable labels can comprise dyes, haptens, chemiluminescent or fluorescent molecules (rhodamine, fluorescein, green fluorescent protein, luciferase), biotin, radiolabels ($^{3}$H, $^{35}$S, $^{32}$P, $^{14}$C, $^{131}$I) enzymes such as alkaline phosphatase or horseradish peroxidase, and the like, as will be understood by those skilled in the art.

The container of the presently-disclosed systems can generally include at least one microtiter plate, well, slide, vial, test tube, flask, bottle, syringe, or other suitable container, into which the antigen can be placed, and, if desired, suitably aliquoted. Where a second or additional binding ligand, such as an antibody preparation, or other component is provided, the system can also include a second, third, or other additional container into which this ligand or component can be placed.

In some embodiments, the antigen can be provided bound to a support, such as, for example, a column matrix, a well of a microtiter plate, a membrane (e.g. nitrocellulose, PVDF, or other suitable material), a polystyrene or other suitable bead, a test tube, or a dip stick. For example, a dip stick can be prepared by coating the pCD antigen on a solid support. This dip stick can then be dipped into the test biological sample and then processed quickly through washes and detection steps to generate a measurable signal, such as for example a colored spot. Alternatively, in some embodiments, the support can be provided as a separate element of the system to allow for further manipulation of the testing conditions, as desired.

In some embodiments, the systems of the presently-disclosed subject matter can further comprise suitable standards or predetermined amounts, including both antibodies and antigens, that can be used to prepare a standard curve for a particular immunoassay.

As noted, the systems of the presently-disclosed subject-matter can be advantageously packaged into a kit comprising the individual components (e.g., the antigen and the means for detecting binding of an autoantibody) and a suitable container. The components of the kits can be packaged either in a liquid solution or in lyophilized form, such as a dried powder. When the components are provided in a liquid solution, the liquid solution can be an aqueous solution. When the reagents are provided in lyophilized form, the dried powder can be reconstituted by the addition of a suitable solvent, which can be further provided.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples. Some of the following examples are prophetic, notwithstanding the numerical values, results and/or data referred to and contained in the examples. Further, the following examples may include compilations of data that are representative of data gathered at various times during the course of development and experimentation related to the presently-disclosed subject matter.

EXAMPLES

Example 1

Synthesis of Antigen

Synthesis of the fragments of the Activation Peptide (AP) that are responsible for binding of procathepsin C (pCD) to the cancer cell surface (i.e., sequences comprising amino acids 36-44 of the AP) was carried out according to well-established protocols (Vagner, et al. 1993), except that the peptides were synthesized as a multiple antigenic peptide (MAP). Briefly peptide synthesis was accomplished by solid-phase peptide synthesis under low-pressure continuous flow conditions using a manually-operated synthesizer. The synthesis was carried out in a flow reactor with adjustable volume using FmocxtBu protection strategy on standard methylbenzhydrylamine polystyrene-based resin. The purity of the peptides was confirmed by amino acid analysis using a Durrum 500 amino acid analyzer and the sequences of the single peptides was confirmed by sequencing using an Applied Biosystems model 470A sequencer. The sequence of the fragment of the AP responsible for binding of pCD to the cancer cell surface is provided as SEQ ID NO:2 (GPVSKYSQAV-PAVTE). The sequence is of the full-length AP is provided as SEQ ID NO: 1 (LVRIPLHKFT SIRRTMSEVG GSV-EDLIAKG PVSKYSQAVP AVTE).

The MAP system utilized the alpha- and gamma-amino functional groups of lysine to form a backbone on which multiple peptide epitopes could be attached. By using this system, it was observed that the lysine core was capable of yielding a MAP bearing four to eight copies of the pCD peptide epitope in a high molar ratio as the inner core generally only accounted for 10% or less of the total molecular weight of the MAP (see, e.g., Wang, et al. 1991; Posnett, et al. 1988; and Tam, 1988). The MAP system did not require a carrier for conjugation, and depending on the number of lysine tiers utilized, different numbers of peptide branches could be synthesized. A 0.1 mmol scale was chosen for synthesis of the MAP in the majority of the experiments because it was observed that this scale yielded maximum coupling during synthesis and thus optimized the preparation of the MAP.

Example 2

Detection of Autoantibodies Immunoreactive to Procathepsin D

Using a MAP, comprised of multiple copies of a fragment of a synthetic activation peptide (AP) from pCD (SEQ ID NO: 2), as an antigen in an ELISA assay, the levels of anti-pCD autoantibodies in serum samples from subjects was measured. The serum samples were obtained from normal, healthy subjects as well as from subjects that had been previously diagnosed with a specific type of cancer. Briefly, the MAP peptide was first dissolved in phosphate-buffered saline (PBS) at 2 mg/ml. From this dilution, a working solution at 0.05 mg/ml in PBS was prepared, which just before each experiment was further diluted in binding solution at pH 9.6 to a concentration of 0.0005 mg/ml. 100 µl of this solution was then used per well of a microtiter plate. After 60 min incubation at 37° C., wells were washed three times with PBS and blocked by incubation with 150 µl of blocking solution (1% bovine serum albumin (BSA) in PBS). After another 60 min incubation 37° C., the wells were again washed three times. Tested sera was diluted in 0.5% BSA in a 1:25 ratio. 100 µl of this solution was applied to each well. After 60 min incubation at 37° C., the wells were washed three times. Following incubation with appropriately diluted anti-human IgG-conjugate, the wells were incubated for 60 min at 37° C., washed three times and incubated with an appropriate substrate for 10 minutes in the dark. After stopping of the reaction, the absorbance was then evaluated on an ELISA reader at an appropriate wavelength depending on substrate utilized.

Figure 2:
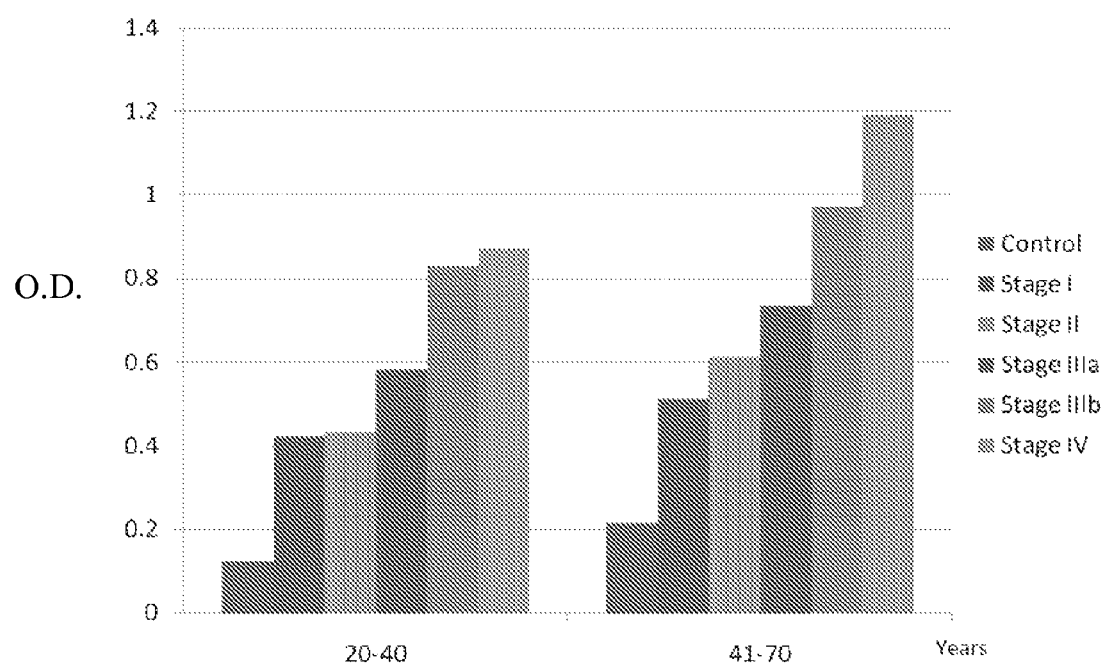
FIG. 2 is a graph depicting levels of anti-procathepsin D autoantibodies detected in serum samples of subjects diagnosed with breast cancer, where the amounts of anti-procathepsin D autoantibodies (y-axis) are plotted against the diagnosed stage of the breast cancer (x-axis) for 20-40 year old subjects and for 41-70 year old subjects.
Figure 3:
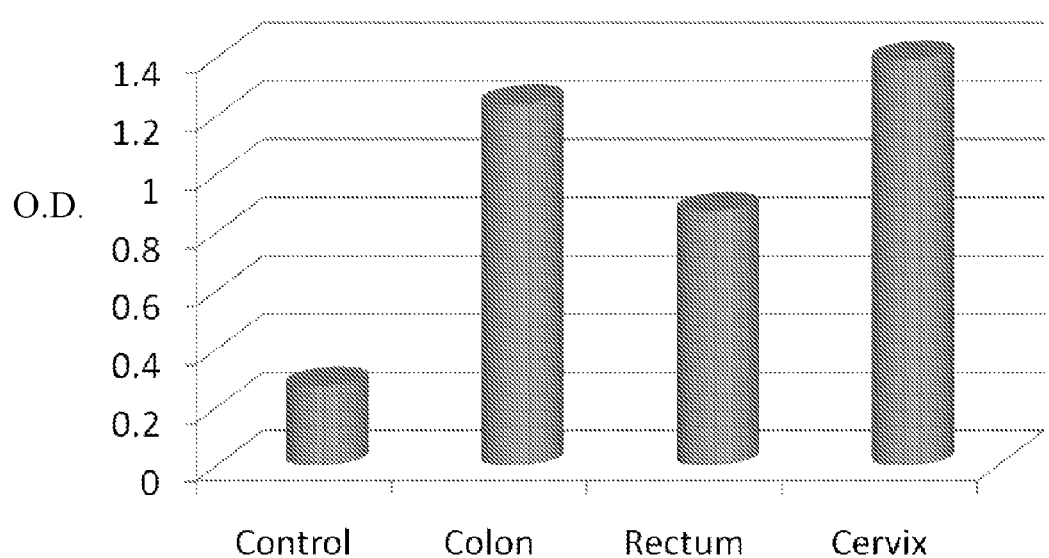
FIG. 3 is a graph depicting levels of anti-procathepsin D autoantibodies detected in serum samples of subjects diagnosed with colon, rectal, or cervical cancer, where the amounts of anti-procathepsin D autoantibodies (y-axis) are plotted against the various types of cancers (x-axis).

As shown in FIGS. 2 and 3, upon analysis of the results from these experiments, it was observed that elevated levels of autoantibodies immunoreactive to pCD were present in serum samples obtained from breast cancer, colon cancer, rectal cancer, and cervical cancer, relative to those levels observed in the control group (15 individual donors without any diagnosis of cancer). These data thus indicate that the level of anti-pCD autoantibodies is elevated in patients with solid tumors, and that these elevated levels can effectively be used for the diagnosis of cancer in a subject.

Since pCD has been reported to be involved in numerous types of cancer, it was thought that specific autoantibodies to pCD can also be found in additional types of cancer. To test this hypothesis, serum samples from patients diagnosed with lung, prostate, and stomach cancer were further tested for elevated levels of the autoantibodies. Results from these experiments again showed elevated levels of anti-pCD autoantibodies, thus further indicating that the autoantibodies can effectively be used to diagnose cancer.

Taken together, these results demonstrate that anti-pCD autoantibodies can serve as a fast, non-invasive and reliable diagnostic technique for the identification of multiple types of cancer.

Example 3

Characterization of Cancer Using Autoantibodies Immunoreactive to Procathepsin D To analyze the ability of the immunodetection methods to characterize a cancer, the anti-pCD autoantibody levels found in Example 2 in serum samples obtained from subjects that had been diagnosed with breast cancer were further analyzed by comparing the levels of anti-pCD autoantibodies with the particular stage of breast cancer that had been diagnosed in each subject. As shown in FIG. 2, upon this further analysis, it was observed that levels of anti-pCD autoantibodies generally increased with each stage of breast cancer and that the elevated levels of anti-pCD autoantibodies, which were observed at each particular stage, could be correlated with the particular stage of breast cancer. As also shown in FIG. 2, these results were observed in samples obtained from subjects that were 20-40 years of age and in samples obtained from subjects that were 41-70 years old, thus indicating that the stage of the breast cancer could be accurately diagnosed in younger subjects as well as older subjects by measuring an amount of anti-pCD autoantibodies.

To further examine the ability of the immunodetection methods to characterize a cancer according to the type and stage of the particular cancer, serum samples from subjects diagnosed with lung cancer, ovarian cancer, colon cancer, rectal cancer, and cervical cancer are obtained and the levels of autoantibodies immunoreactive to pCD are determined in each sample. These levels are correlated with each subject's medical history and diagnosis, including the type of cancer that was diagnosed and the stage of the diagnosed cancer. Elevated levels of autoantibodies immunoreactive to pCD are detected in each type of cancer and these elevated levels are found to be able to be correlated with the particular type of cancer as well as the stage of the particular cancer, thus indicating that the immunodetection methods can effectively be used to characterize multiple cancers, including both the type and stage of the cancer.

Throughout this document, various references are cited. All such references are incorporated herein by reference, including the references set forth in the following list:

REFERENCES

1. Barthell E, Mylonas I, Shabani N, Kunze S, Kuhn C, Jeschke U, Friese K. Immunohistochemical visualization of cathepsin-D expression in breast cancer. *Anticancer Res.* 2007; 27: 2035-2040.
2. Bazzett L B, Watkins C S, Gercel-Taylor C, et al. Modulation of proliferation and chemosensitivity by pCD and its peptides in ovarian cancer. *Gynecol. Oncol.*, 1999; 74: 181-187.
3. Benes P, Koelsch G, Dvorak B, Fusek M, Vetvicka V. Detection of procathepsin D in rat milk. *Comp. Biochem. Physiol.* 2002; 133: 113-118.
4. Benes P, Vashishta A, Saraswat-Ohri S, Fusek M, Pospisilova S, Tichy B, Vetvicka V. Effect of procathepsin D activation peptide on gene expression of breast cancer cells. *Cancer Letters* 2006; 239: 46-54.
5. Fernandez-Aguilar S, Noel J C. Expression of cathepsin D and galectin 3 in tubular carcinomas of the breast. *APMIS* 2008; 116: 33-40.
6. Ferrandina G, Scambia G, Bardelli F, et al. Relationship between cathepsin-D content and disease free survival in node-negative breast cancer patients: A meta-analysis. *Br J. Canc.*, 1997; 76: 661-666.
7. Fusek M, Vetvicka V. Dual Role of Cathepsin D: Ligand and Protease. *Biomed. Papers* 2005; 149(1): 43-50.
8. Fusek M, Vetvicka V. Mitogenic function of human pCD— role of the activation peptide. *Biochem. J.* 1994; 303: 775-780.
9. Fusek M, Vetvickova J and Vetvicka V. Secretion of Cytokines in Breast Cancer Cells: The Molecular Mechanism of Procathepsin D Proliferative Effects. *Journal of Interferon & Cytokine Research* 2007; 27: 191-199.
10. Glondu M, Liaudet-Coopman E, Decrocq D, et al. Down-regulation of cathepsin-D expression by anti-sense gene transfer inhibits tumor growth and experimental lung metastasis of human breast cancer cells. *Oncogene,* 2002; 21: 5127-5134.
11. Harris L, Fritche H, Mennel R, Norton L, Ravdin P, Taube S, Somerfield M R, Hayes, D F, Bast R C. American Society of Clinical Oncology 2007 Update of recommendation for the use of tumor markers in breast cancer. *J. Clin. Oncol.* 2007; 25: 5287-5312.
12. Kaneko I, Tanaka S, Oka S, Yoshida S, Hiyama T, Arihiro K, Shimamoto F, Chayama K. Immunohistochemical molecular markers as predictors of curability of endoscopically resected submucosal colorectal cancer. *World J. Gastroenterol.* 2007; 13:2819-1835.
13. Koelsch G, Metcalf P, Vetvicka V, et al. Human procathepsin D: three-dimensional model and isolation. In: Aspartic Proteinases: Structure, Function, Biology, and Biomedical Implications, K. Takahashi, editor. Plenum Press, New York, 1995, pp. 273-278.
14. Kristek J, Dmitrovic B, Kurbel S, Sakic K, Krajinovic Z, Blazicevic V, Has B, Marjanovic K. Tumor growth fraction, expression of estrogen and progesterone receptors, p53, Bcl-2 and cathepsin D activity in primary ductal invasive breast carcinoma and their axillary lymph node metastases. *Coll. Antropol.* 2007; 4:1043-1047.
15. Leto G, Tumminello F M, Crescimanno M, et al. Cathepsin D expression levels in nongynecological solid tumors: clinical and therapeutical implications. *Clin. Exp. Metastasis,* 2004; 21: 91-106.
16. Lou X, Xiao T, Zhao K, Wang H, Zheng H, Lin D, Lu Y, Gao Y, Cheng S, Liu S, Xu N. Cathepsin D is secreted from M-BE cells: Its potential role as a biomarker of lung cancer. *J. Proteome Res.* 2007; 6: 1083-1092.
17. Minarowska A, Minarowski L, Karwowska A, Sands D, Dabrowska E. The activity of cathepsin D in saliva of cystic fibrosis patients. *Fol. Histol. Cytobiol.* 2007; 45: 165-168.
18. Ohri S, Vashishta A, Proctor M, et al. Depletion of procathepsin D gene expression by RNA interference—A potential therapeutic target for breast cancer. *Cancer Biology and Therapy,* 2007; 6: 1081-1087.
19. Ohri S, Vashishta A, Vetvickova J, Fusek M, Vetvicka V. Procathepsin D expression correlates with invasive and metastatic phenotype of MDA-MB-231 derived cell lines. *In. J. Biol. Macromol.* 2007; 41: 204-209.
20. Posnett D, McGrath H, Tam J P. A novel method for producing anti-peptide antibodies. *J. Biol. Chem.* 1988; 263: 1719-1725.
21. Reid W A, Vallor M J, Kay J. Immunolocalization of cathepsin D in normal and neoplastic tissues. *J. Clin. Pathol.,* 1986; 39: 1323-1330.
22. Saraswat-Ohri S, Vashishta A, Proctor M, Fusek M and Vetvicka V. The propeptide of cathepsin D increases proliferation, invasion and metastasis of breast cancer cells. *International Journal of Oncology* 2008; 32: 491-498.
23. Tam J P. Synthetic peptide vaccine design: synthesis and properties of a high-density multiple antigenic peptide system. *PNAS USA* 1988; 85: 5409-5413.
24. Thorpe S M, Rochefort H, Garcia M, et al. Association between high concentration of 52,000 MW cathepsin D and poor prognosis in primary human breast cancer. *Cancer Res.,* 1989; 49: 6008-6014.
25. Vagner, et al. (1993) *Coll. Czech. Chem. Commun.* 58, 435-444.
26. Vaupel, et al., *Cancer Res.* 49, 6449-6465.

27. Vashishta A, Fusek M, Vetvicka V. Possible role of procathepsin D in human cancer. *Fol. Microbiol.* 2005; 50: 71-76.
28. Vashishta A, Ohri S, Proctor M, et al. Ribozyme-targeting procathepsin D and its effect on invasion and growth of breast cancer cells: An implication in breast cancer therapy. *Int. J. Oncol.*, 2007; 30: 1112-1130.
29. Vashishta A, Ohri S, Proctor M, Fusek M, Vetvicka V. Ribozyme-targeting procathepsin D and its effect on invasion and growth of breast cancer cells: An implication in breast cancer therapy. *Int. J. Oncol.* 2007; 30: 1112-1130.
30. Vashishta A, Saraswat-Ohri S, Proctor M, Fusek M and Vetvicka V. Role of Activation Peptide of Procathepsin D in Proliferation and Invasion of Lung Cancer Cells. *Anticancer Research* 2006; 26: 4163-4170.
31. Vashishta A, Saraswat-Ohri S, Vetvickova J, Fusek M, Ulrichova J, Vetvicka V. Procathepsin D Secreted by HaCaT keratinocyte cells—A novel regulator of keratinocyte growth. *European Journal of Cell Biology* 2007; 86: 303-313.
32. Vetvicka V, Benes P, Fusek M. Procathepsin D in breast cancer: What do we know? Effects of ribozymes and other inhibitors. *Cancer Gene Therapy* 2000; 9: 854-863.
33. Vetvicka V and Fusek M. Procathepsin D and human cancer. *Current Topics in Peptide & Protein Research* Vol. 6, 2004.
34. Vetvicka V, Vetvickova J, Fusek M. Anti-human pCD activation peptide antibodies inhibit breast cancer development. *Breast Cancer Res. Treatment* 1999; 57: 261:269.
35. Vetvicka V, Vetvickova J, Fusek M. Effect of pCD and its activation peptide on prostate cancer cells. *Cancer Lett.,* 1998; 129: 55-59.
36. Vetvicka V, Vetvickova J, Hilgert I, et al. Analysis of the interaction of procathepsin D activation peptide with breast cancer cells. *Int. J. Cancer,* 1997; 73: 403-409.
37. Vetvicka V, Vetvickova V, Benes P. Role of enzymatically inactive pCD in lung cancer. *Int. J. Cancer* 2004; 24: 2739-2744.
38. Vignon F, Capony F, Chambon M, et al. Autocrine growth stimulation of the MCF 7 breast cancer cells by the estrogen-regulated 52 K protein. *Endocrinology* 1986; 118: 1537-1545.
39. Vetvicka V, Vetvickova J, Hilgert I, Voburka Z, Fusek M. Analysis of the interaction of the procathepsin D activation peptide with breast cancer cells, *Int. J. Cancer,* 1997; 73: 403-409.
40. Vetvicka V, Vetvickova J, Fusek M. Role of procathepsin D activation peptide in prostate cancer development. *Prostate* 2000; 44: 1-7.
41. Vetvicka V, Vagner J, Baudys M, Tang J, Foundling S I, Fusek M. Human breast milk contains procathepsin d—detection by specific antibodies. *Biochem. Molec. Biol. Int.* 1993; 30: 921-928.
42. Vetvicka V, Vetvickova J, Benes P. Role of enzymatically inactive procathepsin D in lung cancer. *Anticancer Res.* 2004; 24: 2739-2744.
43. Wang C Y, Looney D J, Li M L, Walfield A M, Ye J, Hosein B, Tam J P, Wong-Staal F. Long-term high-titer neutralizing activity induced by octameric synthetic HIV antigen. *Science* 1991; 254: 285-288.
44. Dowdy and Wearden, Statistics for Research, John Wiley & Sons, New York, 1983.
45. Nakamura, et al. Handbook of Experimental Immunology (4th Ed.), Weir et al. (eds). Vol. 1, Chapter 27, Blackwell Scientific Publ., Oxford, 1987.
46. Molecular Cloning A Laboratory Manual (1989), 2nd Ed., ed. by Sambrook, Fritsch and Maniatis, eds., Cold Spring Harbor Laboratory Press, Chapters 16 and 17.
47. DNA Cloning, Volumes I and II, Glover, ed., 1985.
48. Oligonucleotide Synthesis, M. J. Gait, ed., 1984.
49. Nucleic Acid Hybridization, D. Hames & S. J. Higgins, eds., 1984.
50. Transcription and Translation, B. D. Hames & S. J. Higgins, eds., 1984.
51. Culture Of Animal Cells, R. I. Freshney, Alan R. Liss, Inc., 1987.
52. Immobilized Cells And Enzymes, IRL Press, 1986.
53. Perbal (1984), A Practical Guide To Molecular Cloning.
54. Gene Transfer Vectors For Mammalian Cells, J. H. Miller and M. P. Calos, eds., Cold Spring Harbor Laboratory, 1987.
55. Methods In Enzymology, Vols. 154 and 155, Wu et al., eds., Academic Press Inc., N.Y.
56. Immunochemical Methods In Cell And Molecular Biology (Mayer and Walker, eds., Academic Press, London, 1987.
57. U.S. Pat. No. 3,817,837, to Rubenstein, et al., issued Jun. 18, 1974, and entitled "Enzyme Amplification Assay."
58. U.S. Pat. No. 3,850,752, to Schuurs, et al., issued Nov. 26, 1974, and entitled "Process for the Demonstration and Determination of low Molecular Compounds and of Proteins Capable of Binding These Compounds Specifically."
59. U.S. Pat. No. 3,939,350, to Kronick, et al., issued Feb. 17, 1976, and entitled "Fluorescent Immunoassay Employing Total Reflection for Activation."
60. U.S. Pat. No. 3,996,345, to Ullman, et al., issued Dec. 7, 1976, and entitled "Fluorescence Quenching with Immunological Pairs in Immunoassays."
61. U.S. Pat. No. 4,275,149, to Litman, et al., issued Jun. 23, 1981, and entitled "Macromolecular Environment Control in Specific Receptor Assays."
62. U.S. Pat. No. 4,277,437, to Maggio, issued Jul. 7, 1981, and entitled "Kit for Carrying Out Chemically Induced Fluorescence Immunoassay."
63. U.S. Pat. No. 4,302,534, to Halmann, et al., issued Nov. 24, 1981, and entitled "Chemiluminescent Enzyme Immunoassay."
64. U.S. Pat. No. 4,366,241, to Tom, et al., issued Dec. 28, 1982, and entitled "Concentrating Zone Method in Heterogeneous Immunoassays."
65. U.S. Pat. No. 4,637,988, to Hinshaw, et al., issued Jan. 20, 1987, and entitled "Fluorescent Labels for Immunoassay."
66. U.S. Pat. No. 4,683,195, to Mullis, et al., issued Jul. 28, 1987, and entitled "Process for Amplifying, Detecting, and/or Cloning Nucleic Acid Sequences."
67. U.S. Pat. No. 4,786,594, to Khanna, et al., issued Nov. 22, 1988, and entitled "Enzyme Immunoassay."
68. U.S. Pat. No. 5,108,896, to Philo, et al., issued Apr. 28, 1992, and entitled "Simultaneous Immunoassay of Two Analytes Using Dual Enzyme Labeled Antibodies."
69. U.S. Pat. No. 5,229,302, to Miyazaki, et al., issued Jul. 20, 1993, and entitled "Fluorescence Immunoassay Method Utilizing Pseudo-Antigens Combined with Fluorescent Quenchers."
70. U.S. Pat. No. 5,629,164, to Rivers, issued May 13, 1997, and entitled "Enzyme Immunoassay Device."
71. U.S. Pat. No. 5,691,154, to Callstrom, et al., issued Nov. 25, 1997, and entitled "Enzyme Linked Immunoassay with Stabilized Polymer Saccharide Enzyme Conjugates."
72. U.S. Pat. No. 5,800,814 to Fusek, et al., issued Sep. 1, 1998, and entitled "Method for Inhibition of Breast Tumor Growth."

It will be understood that various details of the presently-disclosed subject matter can be changed without departing from the scope of the subject matter disclosed herein. Furthermore, the foregoing description is for the purpose of illustration only, and not for the purpose of limitation.

What is claimed is:

1. A method for determining an amount of autoantibodies immunoreactive to an antigen present in a biological sample of a subject, comprising:
   providing a biological sample from the subject;
   contacting an antigen with the biological sample, wherein the antigen consists of a peptide of SEQ ID NO:2, or consists of a plurality of peptides of SEQ ID NO: 2;
   detecting the autoantibodies in the sample immunoreactive to the antigen; and
   determining an amount in the sample of autoantibodies immunoreactive to procathepsin D (pCD) based on the autoantibodies detected.

2. The method of claim 1, wherein the biological sample comprises blood, plasma, serum, urine, cerebrospinal fluid, saliva, or breast milk.

3. The method of claim 1, wherein the antigen consists of a plurality of peptides of SEQ ID NO: 2.

4. The method of claim 1, further comprising determining the subject may have cancer by comparing the amount of the autoantibodies in the sample, if present, to a control level of the autoantibodies, wherein the subject is determined to have the cancer if there is a measurable difference in the amount of the autoantibodies in the sample as compared to the control level.

5. The method of claim 4, wherein the cancer is selected from the group consisting of breast cancer, lung cancer, ovarian cancer, colon cancer, rectal cancer, and cervical cancer.

6. The method of claim 5, wherein the cancer is breast cancer.

7. The method of claim 4, further comprising selecting a treatment or modifying a treatment for the cancer based on the determined amount of the autoantibodies.

8. The method of claim 4, further comprising characterizing a cancer based on the determined amount of autoantibodies.

9. The method of claim 8, wherein characterizing the cancer comprises determining a stage of the cancer.

* * * * *

SEQUENCE LISTING

```
<160> NUMBER OF SEQ ID NOS: 2

<210> SEQ ID NO 1
<211> LENGTH: 44
<212> TYPE: PRT
<213> ORGANISM: Homo sapiens

<400> SEQUENCE: 1

Leu Val Arg Ile Pro Leu His Lys Phe Thr Ser Ile Arg Arg Thr Met
1               5                   10                  15

Ser Glu Val Gly Gly Ser Val Glu Asp Leu Ile Ala Lys Gly Pro Val
            20                  25                  30

Ser Lys Tyr Ser Gln Ala Val Pro Ala Val Thr Glu
        35                  40

<210> SEQ ID NO 2
<211> LENGTH: 15
<212> TYPE: PRT
<213> ORGANISM: Homo sapiens

<400> SEQUENCE: 2

Gly Pro Val Ser Lys Tyr Ser Gln Ala Val Pro Ala Val Thr Glu
1               5                   10                  15
```